(12) United States Patent
Song et al.

(10) Patent No.: US 9,353,207 B2
(45) Date of Patent: May 31, 2016

(54) ALKYLPHENYL DERIVATIVES AND APPLICATION THEREOF AS PHOTOINITIATOR

(71) Applicant: HUIZHOU HUAHONG NEW MATERIAL CO., LTD., Guangdong (CN)

(72) Inventors: Senchuan Song, Guangdong (CN); Jianxiong Lin, Guangdong (CN); Chuanwen Chen, Guangdong (CN); Jianghan Chen, Guangdong (CN); Zhaojiang Liu, Guangdong (CN); Xuefei Zheng, Guangdong (CN); Jianan Hou, Guangdong (CN); Wandong Li, Guangdong (CN)

(73) Assignee: HUIZHOU HUAHONG NEW MATERIAL CO., LTD., Huizhou, Guangdong Province (CN)

( * ) Notice: Subject to any disclaimer, the term of this patent is extended or adjusted under 35 U.S.C. 154(b) by 0 days.

(21) Appl. No.: 14/654,145

(22) PCT Filed: Dec. 20, 2013

(86) PCT No.: PCT/CN2013/090166
§ 371 (c)(1),
(2) Date: Jun. 19, 2015

(87) PCT Pub. No.: WO2014/094658
PCT Pub. Date: Jun. 26, 2014

(65) Prior Publication Data
US 2015/0329662 A1    Nov. 19, 2015

(30) Foreign Application Priority Data
Dec. 23, 2012 (CN) .......................... 2012 1 0566735

(51) Int. Cl.
*C08F 2/50* (2006.01)
*C08F 2/46* (2006.01)
*C08G 61/04* (2006.01)
*C08F 224/00* (2006.01)
*C07D 211/14* (2006.01)
*C07D 295/108* (2006.01)
*C07D 295/104* (2006.01)
*C09D 163/10* (2006.01)
*C08G 59/68* (2006.01)

(52) U.S. Cl.
CPC ............ *C08F 224/00* (2013.01); *C07D 211/14* (2013.01); *C07D 295/104* (2013.01); *C07D 295/108* (2013.01); *C08F 2/50* (2013.01); *C08G 59/68* (2013.01); *C09D 163/10* (2013.01)

(58) Field of Classification Search
None
See application file for complete search history.

(56) References Cited

U.S. PATENT DOCUMENTS 4,321,118 A    3/1982    Felder et al.
4,992,547 A    2/1991    Berner et al.

FOREIGN PATENT DOCUMENTS

CN    103012317 A    4/2012

OTHER PUBLICATIONS

International Preliminary Report on Patentability issued Jun. 23, 2015 in International Application PCT/CN2013/090166.
International Search Report mailed on Mar. 27, 2014 in International Application PCT/CN2013/090166.

*Primary Examiner* — Ling Choi
*Assistant Examiner* — Jessica E Whiteley
(74) *Attorney, Agent, or Firm* — Pillsbury Winthrop Shaw Pittman LLP

(57) ABSTRACT

The invention provides novel compounds, namely tert-butylphenyl-2-methyl-2-(1-piperidyl)-1-acetone and tert-butylphenyl-2-methyl-2-(1-morpholinyl)-1-acetone, and the preparation method thereof and the use thereof as a photoinitiator. The invention further provides a photopolymerizable composition comprising the compound as the photoinitiator and the use thereof, and provides a coating substrate coated with the composition.

7 Claims, No Drawings

ALKYLPHENYL DERIVATIVES AND APPLICATION THEREOF AS PHOTOINITIATOR

CROSS REFERENCE TO RELATED APPLICATION

This application is a national stage application, filed under 35 U.S.C. §371, of PCT Application No. PCT/CN2013/090166, filed on Dec. 20, 2013, entitled "ALKYLPHENYL DERIVATIVES AND APPLICATION THEREOF AS PHOTOINITIATOR", which claimed priority to Chinese Application No. 201210566735.1, filed on Dec. 23, 2012, all of which are hereby incorporated by reference in their entirety.

FIELD OF THE INVENTION

The present invention relates to the technical field of photoinitiator agent. Specifically, the present invention provides new alkylphenyl derivatives and the preparation thereof, and the use thereof as photoinitiators.

BACKGROUND OF THE INVENTION

Photoinitiators, also known as a photosensitizer or photo-curing agent, is a kind of compounds absorbing certain wavelengths of energy in the range of the UV region (250~420 nm) or visible light region (400~800 nm) to generate free radicals or cations, causing monomers crosslinking. Radiation curing technology is a new energy-saving technology. Curing by ultraviolet (UV) and electron beam (EB), infrared light, visible light, laser, chemical fluorescence radiation, is in full compliance with "5E" Features: Efficient (efficiency), Enabling (utility), Economical (economy), Energy Saving (saving), Environmental Friendly (environmentally friendly), therefore is deemed as the "green technology". Photoinitiator is one of the important components of a photo-curing adhesive, whose cure rate plays a decisive role. After the photoinitiator agent is irradiated by UV, it absorbs light energy and splits into two active free radicals, triggering photosensitive resin and reactive diluents chain polymerization, so that the adhesive crosslinks. It is rapid, environmental protection, energy saving.

In these days, the photoinitiators have been widely used in paintings, ink industry. With the improvement of people's living standards, the environment and food safety issues get more attention. Packaging industry, especially color printing in the food packaging industry, harmful volatile organic compounds (VOC), such as benzene, carbon tetrachloride, chloroform, etc., are now with clear limitations. Photoinitiators used for the food sector in the past, such as benzophenone, stilbene dione, which produce benzene during the use, have been banned from use in food-related printing industry. In addition, the present photoinitiators can not meet the requirements of the users because of their performance or price.

Therefore, in the photopolymerization technology field, it is still needed to have a photoinitiator with higher activity, readier to be prepared and handled. The present invention surprisingly found that, the new compounds 1-(4-tert-butyl-phenyl)-2-methyl-2-(1-piperidyl)-1-acetone and 1-(4-tert-butyl-phenyl)-2-methyl-2-(1-morpholinyl)-1-acetone are extremely effective photoinitiator, and in comparison with the existing photoinitiators, especially the widely used 2-benzyl-2-(dimethylamino)-1-[4-(4-morpholinyl)phenyl]-1-butanone, production costs are significantly reduced, while the production process is much simpler, post-treatment is much simpler, therefore meet the environment protection requirements.

DETAILED DESCRIPTION OF THE INVENTION

The present invention provides a compound of formula

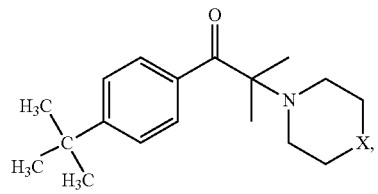

wherein X is C or O.

In one respect of the present invention, the compound is:

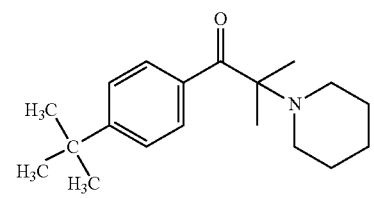 [SMILES: CC(C)(C)c1ccc(C(=O)C(C)(C)N2CCCCC2)cc1]

1-(4-tert-butyl-phenyl)-2-methyl-2-(1-piperidyl)-1-acetone

In one respect of the present invention, the compound is:

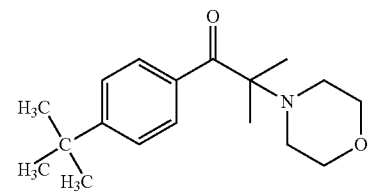

1-(4-tert-butyl-phenyl)-2-methyl-2-(1-morpholinyl)-1-acetone

The present invention provides a process for synthesizing a compound of formula

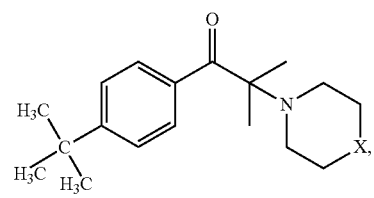

wherein X is C or O, which includes the following steps:

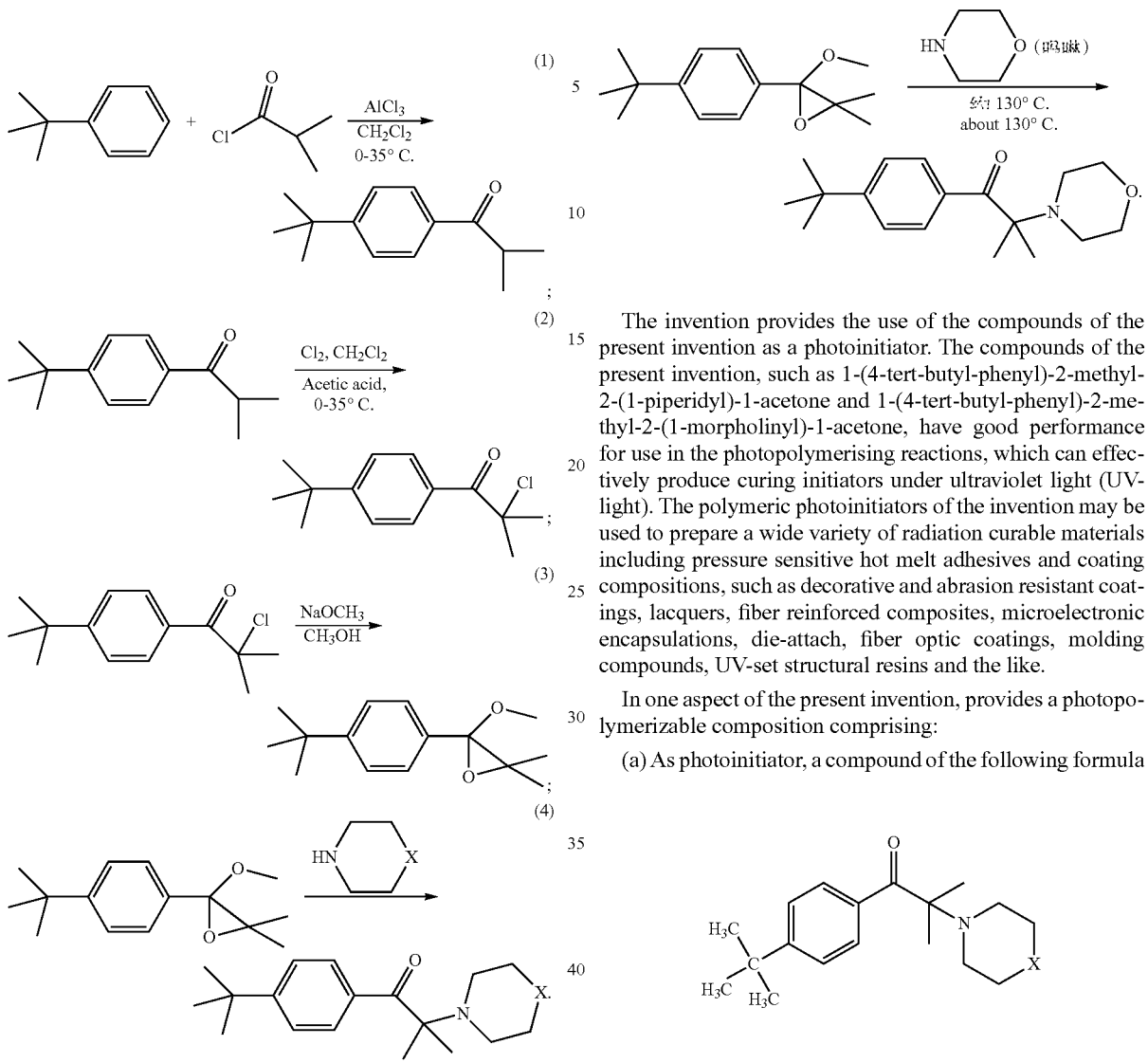

In one respect of the present invention, the reaction temperature in Step (4) is about 130° C.

In one respect of the present invention, in preparing 1-(4-tert-butyl-phenyl)-2-methyl-2-(1-piperidyl)-1-acetone, Step (4) is

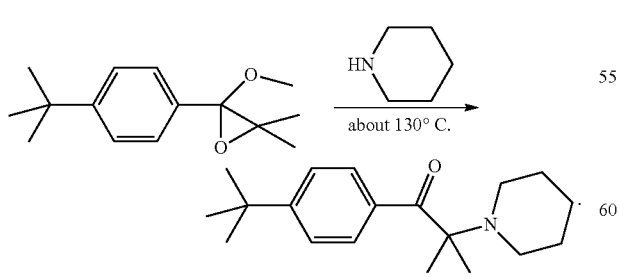

In one respect of the present invention, in preparing 1-(4-tert-butyl-phenyl)-2-methyl-2-(1-morpholinyl)-1-acetone, Step (4) is The invention provides the use of the compounds of the present invention as a photoinitiator. The compounds of the present invention, such as 1-(4-tert-butyl-phenyl)-2-methyl-2-(1-piperidyl)-1-acetone and 1-(4-tert-butyl-phenyl)-2-methyl-2-(1-morpholinyl)-1-acetone, have good performance for use in the photopolymerising reactions, which can effectively produce curing initiators under ultraviolet light (UV-light). The polymeric photoinitiators of the invention may be used to prepare a wide variety of radiation curable materials including pressure sensitive hot melt adhesives and coating compositions, such as decorative and abrasion resistant coatings, lacquers, fiber reinforced composites, microelectronic encapsulations, die-attach, fiber optic coatings, molding compounds, UV-set structural resins and the like.

In one aspect of the present invention, provides a photopolymerizable composition comprising:

(a) As photoinitiator, a compound of the following formula

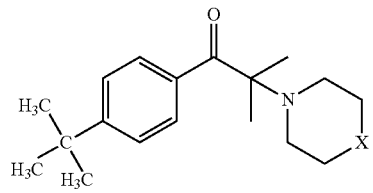

wherein X is C or O; and (b) At least one ethylenically unsaturated photopolymerizable compound.

In a further aspect of the present invention, the photoinitiator in said photopolymerizable composition is:

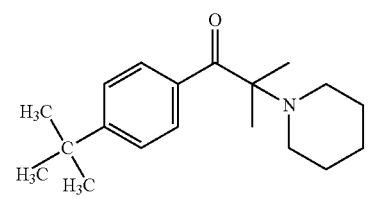 [SMILES: CC(C)(C)c1ccc(C(=O)C(C)(C)N2CCCCC2)cc1]

1-(4-tert-butyl-phenyl)-2-methyl-2-(1-piperidyl)-1-acetone

In a further aspect of the present invention, the photoinitiator in said photopolymerizable composition is:

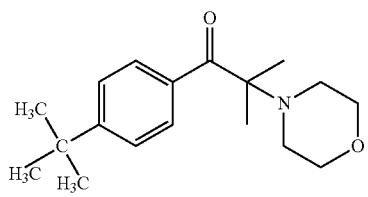 [SMILES: CC(C)(C)c1ccc(C(=O)C(C)(C)N2CCOCC2)cc1]

1-(4-tert-butyl-phenyl)-2-methyl-2-(1-morpholinyl)-1-acetone

In one aspect of the present invention, the photopolymerizable composition can further comprise other known photoinitiator. Common known photoinitiators include those such as camphor quinone, benzophenone, benzophenone derivatives, acetophenone, acetophenone derivatives, benzil ketals, phenylglyoxalic esters and derivatives thereof, diacetyl, peresters.

In one aspect of the present invention, the photoinitiators of the invention will typically be used in amounts of about 0.5-20%, preferably about 1-10%, most preferably about 3-6% by weight based on the weight of the photopolymerizable composition. If the composition contains a mixture of photoinitiators, the amount is the amount of photoinitiator (a) or photoinitiator (a) plus the other photoinitiators. The concentration is chosen based on the thickness of the application of curable composition. Combinations of two or more photoinitiators may also be used to achieve the best possible cure of the formulated compositions. Photoinitiators are preferably used in the least amount necessary to get initiation of cure at the line speed of the process and desired strength for the end use contemplated. This amount will be dependent on the polymeric composition, as well as the source of radiation, the amount of radiation received, the production line speed, and the thickness of the coating on the substrate.

In one aspect of the present invention, said ethylenically unsaturated photopolymerizable compound in component (b) is known in the art. In general, said ethylenically unsaturated photopolymerizable compound may include one or more olefinic double bonds. Examples of monomers containing a double bond are alkyl, hydroxyalkyl or amino acrylates, or alkyl, hydroxyalkyl methacrylates. Examples of monomers containing two or more double bonds are the diacrylates of ethylene glycol, propylene glycol, neopentyl glycol, hexamethylene glycol or of bisphenol A, and 4,4'-bis(2-acryl-oyloxyethoxy)diphenylpropane and the like.

In one aspect of the present invention, said ethylenically unsaturated photopolymerizable compound in component (b) is esters of ethylenically unsaturated carboxylic acids and polyols or polyepoxides. Examples of unsaturated carboxylic acids are acrylic acid, methacrylic acid, and unsaturated fatty acids such as linolenic acid or oleic acid. Acrylic and methacrylic acid are preferred.

Said ethylenically unsaturated photopolymerizable compound in component (b) can be one compound thereof, or a mixture of two or more compounds.

In one aspect of the present invention, said ethylenically unsaturated photopolymerizable compound is acrylated epoxy resins, alkyl acrylates or mixtures thereof, preferably is epoxy acrylate, trimethylolpropane triacrylate or mixtures thereof.

In the photopolymerizable composition of the present invention, the ethylenically unsaturated photopolymerizable compound of component (b) will typically be used in amounts of about 10% to about 70%, preferably about 25% to about 60%, most preferably about 29% to about 56%.

Said photopolymerizable composition of the present invention can further contain other additives (c).

In one aspect of the present invention, said additives (c) in the photopolymerizable composition of the present invention is reactive amine co-initiator, for example water-soluble tertiary amines, such as triethanolamine, N-methyl-diethanolamine, N'N'-dimethyl-ethanolamine, and the like. In the photopolymerizable composition of the present invention, the reactive amine will typically be used in amounts of about 0.5-10%, preferably about 6-10% by weight of the composition.

Other additives can be present in the photopolymerizable composition of the present invention include thermal inhibitors, examples being hydroquinone, hydroquinone derivatives, p-methoxyphenol, β-naphthol or sterically hindered phenols. To exclude atmospheric oxygen during the polymerization it is possible to add paraffin or similar wax-like substances. Light stabilizers which can be added in a small quantity are UV absorbers, for example those of the hydroxyphenylbenzotriazole, hydroxyphenyl-benzophenone, oxalamide or hydroxyphenyl-s-triazine type.

Further additives known in the art includes flow improvers, adhesion promoters. The choice of additive(s) is made depending on the field of application and on properties required for this field. The additives described above are customary in the art and accordingly are added in amounts which are usual in the respective application.

In one aspect, the present invention provides a photopolymerizable composition comprising:

| | |
|---|---|
| epoxy acrylate | about 35-55% |
| amine co-initiator | about 6-10% |
| trimethylolpropane triacrylate | about 29-56% |
| photoinitiator | about 3-6%. |

The photosensitivity of the photopolymerizable compositions of the present invention includes 190-600 nm (UV-vis region). Suitable radiation is present in sunlight or light from artificial light sources. Consequently, a large number of very different types of light sources are employed. The distance between the lamp and the substrate to be exposed in accordance with the invention may vary depending on the intended application and the type and output of lamp. Lasers in the visible region can also be employed.

The present invention provides a coating substrate of at least one of its faces is coated with the photopolymerizable compositions of the present invention. The photopolymerizable compositions are suitable, for example, as coating materials for substrates of all kinds which are in need of protection, for example wood, textiles, paper, ceramics, glass, plastics such as polyesters, polyethylene terephthalate, polyolefins or cellulose acetate, especially in the form of films, and also metals such as Al, Cu, Ni, Fe, Zn, Mg or Co and GaAs, Si or SiO2, by means of imagewise exposure, to generate an image.

The present invention provides the use of the aforementioned photopolymerizable compositions, including for producing pigmented and non-pigmented paints and varnishes, powder coatings, printing inks, printing plates, adhesives, photoresists for electronics, as composition for encapsulating electrical and electronic components, for producing magnetic recording materials, micromechanical parts, waveguides, optical switches, plating masks, etch masks, color proofing systems, glass fiber cable coatings, screen printing stencils, for producing three-dimensional objects by means of stereolithography, and as image recording material, especially for holographic recordings, microelectronic circuits, decolorizing materials for image recording materials, for image recording materials using microcapsules.

EXAMPLES

The following examples are provided for illustrative purposes only.

Example 1

Synthesis of 1-(4-tert-butyl-phenyl-2-methyl-2-(1-piperidyl)-1-acetone and 1-(4-tert-butyl-phenyl)-2-methyl-2-(1-morpholinyl)-1-acetone The scheme for the synthesis of 1-(4-tert-butyl-phenyl)-2-methyl-2-(1-piperidyl)-1-acetone and 1-(4-tert-butyl-phenyl)-2-methyl-2-(1-morpholinyl)-1-acetone include the following steps:

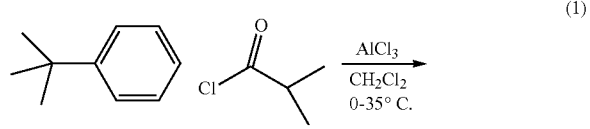

(1)

(2)

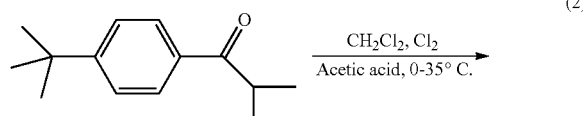

(3)

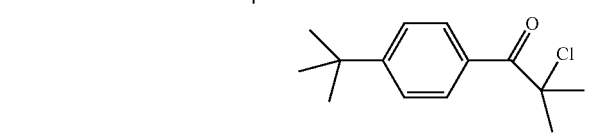

(4)

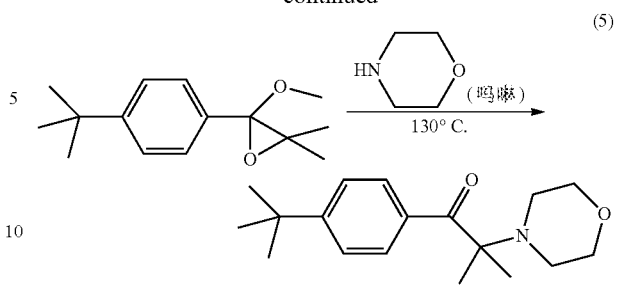

(5)

(1) Synthesis of 1-(4-tert-butyl-phenyl)-2-methyl-1-acetone

To a 1000 mL three-necked flask, 500 mL methylene dichloride and 167.9 g (1.25 mol) aluminum chloride were added. 127.8 g (1.2 mol) isobutyryl chloride was added at 25-30° C. Cooled with ice water to 0-5° C. 134 g (1.0 mol) t-butyl benzene was added drop-wisely. After that, the cooling device was removed and the temperature was raised to room temperature, the reaction was continued for 2-3 hours (HPLC analysis shows the content was 98%).

To a 2000 mL flask, 700 mL water and 50 mL of concentrated hydrochloric acid was added and uniformly mixed, then cooled to 10-15° C. The reaction mixture was added dropwise with stirring to the aqueous hydrochloric acid, maintaining the temperature not higher than 30° C. Removing aluminum trichloride by hydrolysis. After the hydrolysis, it was allowed to stand for 30 minutes, the aqueous phase was separated, the organic phase was washed twice with 300 mL water. After dried, the solvent was distilled to remove dichloromethane to give 1-(4-tert-butylphenyl)-2-methyl-1-acetone. $^1$H NMR (300 Hz, CDCl$_3$), δ: 0.75 (d, J=4.2 Hz, 6H), 0.88 (s, 9H), 3.06-3.12 (m, 1H), 6.99-7.03 (m, 2H), 7.42-7.47 (m, 2H).

(2) Synthesis of 1-(4-tert-butyl-phenyl)-2-methyl-2-chloro-1-acetone

To a 2000 mL three-necked flask, 200 mL methylene dichloride, 100 mL of glacial acetic acid and 1.0 mol (204.3 g) of 1-(4-tert-butylphenyl)-2-methyl-1-acetone were added. Chlorine gas was slowly input for 2.5-4.0 hours when the temperature is controlled to be at 25-30° C. Monitoring the reaction by thin layer liquid chromatography (TLC) until the chlorination reaction was complete. Using HPLC to detect 1-(4-tert-butylphenyl)-2-methyl-1-acetone was completely reacted. The content of the synthesized 1-(4-tert-butylphenyl)-2-chloro-1-methyl-2-acetone was 95%.

Under cooling, a 30% sodium hydroxide solution was added dropwise with stirring to neutral the pH value of the above reaction mixture. Allowing it to be standing still and separated. The organic layer was extracted twice with 50 mL of dichloromethane. The organic layers were combined, dried and then distilled to remove dichloromethane to give 1-(4-tert-butylphenyl)-2-methyl-2-chloro-1-acetone. $^1$HNMR (300 Hz, CDCl$_3$), δ: 1.36 (s, 9H), 2.96 (s, 6H), 7.43-7.46 (m, 2H), 8.10-8.14 (m, 2H).

(3) Synthesis of 2-(4-tert-butyl-phenyl)-2-methoxy-3,3-dimethylethylene oxide

In a 1000 mL three-necked flask, 650 mL of anhydrous methanol and 27.6 g (1.2 mol) of metallic sodium were added to prepare a methanol solution of sodium methylate. 238.7 g (1.0 mol) 1-(4-tert-butyl-phenyl)-2-methyl-2-chloro-1-acetone was added portion-wisely within 1.5-2.0 hours while the temperature was controlled at 25-30° C. After completion of the drop-wisely addition, reaction was continued for 1 hour. Using HPLC to detect 1-(4-tert-butylphenyl)-2-chloro-1-methyl-2-acetone was completely reacted. The content of the synthesized 2-(4-tert-butyl-phenyl)-2-methoxy-3,3-dimethylethylene oxide was 90%.

Using rotary distillation, 60° C., to remove methanol and then cooled to give a white solid substance, which was a mixture of 2-(4-tert-butyl-phenyl)-2-methoxy-3,3-dimethylethylene oxide and sodium chloride.

The purified 2-(4-tert-butyl-phenyl)-2-methoxy-3,3-dimethylethylene oxide: $^1$H NMR (300 Hz, CDCl$_3$), δ: 1.12 (s, 6H), 1.55 (s, 9H), 3.42 (s, 3H), 7.35-7.42 (m, 4H).

(4) Synthesis of 1-(4-tert-butyl-phenyl)-2-methyl-2-(1-piperidyl)-1-acetone

In a 1000 mL three-necked flask, 117.2 g (0.5 mol) 2-(4-tert-butyl-phenyl)-2-methoxy-3,3-dimethylethylene oxide and 255 g (3.0 mol) piperidine was added and heated at reflux until 2-(4-tert-butyl-phenyl)-2-methoxy-3,3-dimethylethylene oxide was reacted completely detecting by HPLC. The content of the synthesized 1-(4-tert-butyl-phenyl)-2-methyl-2-(1-piperidyl)-1-acetone was 96%.

Using rotary distillation, 120° C., to remove excess piperidine. After cooling, 300 mL of toluene was added, stirred, allowed to stand, and filtered. The solid was then treated with 100 mL toluene twice. The combined organic layer was washed twice with 200 mL of water, and then was added 5 g of activated carbon, reflux for 10 minutes to decolorize. Filtering and using rotary distillation, 110° C., to remove toluene to give a light yellow liquid of 1-(4-tert-butylphenyl)-2-methyl-2-(1-piperidinyl)-1acetone. $^1$H NMR (300 Hz, CDCl$_3$), δ: 1.30 (s, 6H), 1.36 (s, 9H), 1.45-1.50 (m, 2H), 1.54-1.57 (m, 4H), 2.53 (t, J=5.1 Hz, 4H), 7.42-7.46 (m, 2H), 8.60 (d, J=8.7 Hz, 2H). MS m/z (C$_{19}$H$_{30}$NO=288.2, i.e., M+H)$^+$⅓ 288.2.

(5) Synthesis of 1-(4-tert-butyl-phenyl)-2-methyl-2-(1-morpholinyl)-1-acetone In a 1000 mL three-necked flask, 117.2 g (0.5 mol) 2-(4-tert-butyl-phenyl)-2-methoxy-3,3-dimethylethylene oxide and 261 g (3.0 mol) morpholine was added and heated at reflux until 2-(4-tert-butyl-phenyl)-2-methoxy-3,3-dimethylethylene oxide was reacted completely detecting by HPLC. The content of the synthesized 1-(4-tert-butyl-phenyl)-2-methyl-2-(1-morpholinyl)-1-acetone was 93%.

Using rotary distillation, 120° C., to remove excess morpholine. After cooling, 300 mL of toluene was added, stirred, allowed to stand, and filtered. The solid was then treated with 100 mL toluene twice. The combined organic layer was washed twice with 200 mL of water, and then was added 5 g of activated carbon, reflux for 10 minutes to decolorize. Filtering and using rotary distillation, 110° C., to remove toluene to give a light yellow liquid of 1-(4-tert-butylphenyl)-2-methyl-2-(1-morpholinyl)-1acetone. $^1$H NMR (300 Hz, CDCl$_3$), δ: 1.32 (s, 6H), 1.38 (s, 9H), 2.58 (t, J=6.9 Hz, 4H), 3.70 (t, J=6.9 Hz, 4H), 7.43 (J=8.7 Hz, 2H), 8.60 (d, J=8.7 Hz, 2H). MS m/z (C$_{18}$H$_{28}$NO=290.2, i.e., M+H)$^+$⅓ 290.2.

It was found during the process that, in step (2), to use the bromination reaction, i.e., using Br$_2$ instead of Cl$_2$ as reactants, it not only increased costs, but also resulted in significantly reduced yield, under certain conditions, it even can not generate the desired product.

Example 2

Preparation of Varnish Formulation

Ultraviolet light curable varnish formulation is prepared according to the following formula.

The formulation is:

| component | % by weight over the composition |
|---|---|
| epoxy acrylate | about 35-55% |
| acrylated aliphatic tertiary amine P115 | about 6-10% |
| trimethylolpropane triacrylate | about 29-56% |
| photoinitiator | about 3-6%. |

1-(4-tert-butyl-phenyl)-2-methyl-2-(1-piperidyl)-1-acetone, 1-(4-tert-butyl-phenyl)-2-methyl-2-(1-morpholinyl)-1-acetone and 2-benzyl-2-(dimethylamino)-1-[4-(4-morpholinyl)phenyl]-1-butanone is used as the photoinitiator respectively in the above formulation to give invention formulation 1, invention formulation 2 and comparison formulation.

Example 3

Curing Test

Varnish formulations prepared in Example 2 were painted on a blank sheet of paper with a printability tester, the coating thickness is about 15 microns. Cured with a medium pressure mercury arc lamp of 50 W/CM line power at 100 m/min, recording the number of times required for obtaining good surface and thorough curing.

| Varnish formulation | photoinitiator | the number of times required for thorough curing |
|---|---|---|
| invention formulation 1 | 1-(4-tert-butyl-phenyl)-2-methyl-2-(1-piperidyl)-1-acetone | 3 |
| invention formulation 2 | 1-(4-tert-butyl-phenyl)-2-methyl-2-(1-morpholinyl)-1-acetone | 3 |
| comparison formulation 1 | 2-benzyl-2-(dimethylamino)-1-[4-(4-morpholinyl)phenyl]-1-butanone | 5 |
| comparison formulation 2 | 1-(4-methylphenyl)-2-methyl-2-(1-piperidyl)-1-acetone | 5 |

The results showed that the varnish formulations using the compounds of the present invention, i.e., 1-(4-tert-butyl-phenyl)-2-methyl-2-(1-piperidyl)-1-acetone and 1-(4-tert-butyl-phenyl)-2-methyl-2-(1-morpholinyl)-1-acetone as photoinitiator have a faster curing rate than the varnish formulations using 2-benzyl-2-(dimethylamino)-1-[4-(4-morpholinyl)phenyl]-1-butanone or 1-(4-methylphenyl)-2-methyl-2-(1-piperidyl)-1-acetone as photoinitiator.

Example 4

Yellowing Resistance Test

Varnish formulations prepared in Example 2 were painted on a blank sheet of paper with a printability tester, the coating thickness is about 15 microns. Cured with a medium pressure mercury arc lamp of 50 W/CM line power at 100 m/min for 4 times. The color change of the cured films were observed with a gray scale card, which contains 1-5 levels: the best level is 5, representing basically no color change; level 3 and below 3 representing obvious color change.

| varnish formulation | photoinitiator | Yellowing resistency level |
| --- | --- | --- |
| invention formulation 1 | 1-(4-tert-butyl-phenyl)-2-methyl-2-(1-piperidyl)-1-acetone | 4 |
| comparison formulation 2 | 1-(4-methylphenyl)-2-methyl-2-(1-piperidyl)-1-acetone | 2 |

Example 5

Benzene Releasing Test

Determination of the amount of benzene emissions by the cured film by head-space gas chromatography:
1) Quantitative Analysis Curve Plotting
  1. 20 mg benzene was added to a 250 ml volumetric flask, accurately weighed (accurate to 0.1 mg), glyceryl triacetate is added for constant volume, this is Level 1 standard solution;
  2. 50.00 ml Level 1 standard solution was added to a 250 ml volumetric flask, accurately weighed (accurate to 0.1 mg), glyceryl triacetate is added for constant volume, this is Level 2 standard solution;
  3. 50.00 ml Level 2 standard solution was added to a 250 ml volumetric flask, accurately weighed (accurate to 0.1 mg), glyceryl triacetate is added for constant volume, this is Level 3 standard solution;
  4. 50.00 ml Level 3 standard solution was added to a 250 ml volumetric flask, accurately weighed (accurate to 0.1 mg), glyceryl triacetate is added for constant volume, this is Level 4 standard solution;
  5. 50.00 ml Level 4 standard solution was added to a 250 ml volumetric flask, accurately weighed (accurate to 0.1 mg), glyceryl triacetate is added for constant volume, this is Level 5 standard solution;
  6. 1000 uL Level 1-5 standard solutions were taken for headspace-gas chromatography analysis, repeated the measurements for every level standard solution twice and took averaged. Based on the peak area and the benzene content (the standard concentration is converted to be the mass content of benzene per unit area of the film, $mg/m^2$), established a working curve through the origin point.
2) Sample Preparation and Measurement The solid membrane was prepared from the varnish formulations was peeled from the glass plate, clipping to obtain a 100 $cm^2$ piece, putting into a vial, adding 1000 uL glyceryl triacetate, headspace-gas chromatography analysis, conducted emission calculation according to the peak area of benzene and the slope K of the curve, formula: C=A/K.
3) Measurement Result:

| Photoinitiator used to cure sample membrane | Benzene emission from the cured sample membrane ($mg/m^2$) |
| --- | --- |
| 1-(4-tert-butylphenyl)-2-methyl-2-(1-piperidinyl)-1-propanone | 0.005 |
| 1-(4-tert-butyl-phenyl)-2-methyl-2-(1-morpholinyl)-1-acetone | 0.002 |

The inventors of the present invention surprisingly found that, the novel compounds, 1-(4-tert-butyl-phenyl)-2-methyl-2-(1-piperidyl)-1-acetone and 1-(4-tert-butyl-phenyl)-2-methyl-2-(1-morpholinyl)-1-acetone, have good performance for use in the photopolymerizing reactions, which can effectively produce polymerizing initiators under ultraviolet light (UV-light). The formulation tests showed that the varnish formulations using the compounds of the present invention, i.e., 1-(4-tert-butyl-phenyl)-2-methyl-2-(1-piperidyl)-1-acetone and 1-(4-tert-butyl-phenyl)-2-methyl-2-(1-morpholinyl)-1-acetone as photoinitiator can meet the environmental requirements and have a faster curing rate than the varnish formulations using 2-benzyl-2-(dimethylamino)-1-[4-(4-morpholinyl)phenyl]-1-butanone as photoinitiator and in comparison with the existing photoinitiators, especially the widely used 2-benzyl-2-(dimethylamino)-1-[4-(4-morpholinyl) phenyl]-1-butanone, production costs are significantly reduced, while the production process is much simpler, post-treatment is much simpler, therefore meet the environment protection requirements.

Unless otherwise indicated, the practice of the present invention will employ common technologies of organic chemistry, polymer chemistry, and the like. It is apparently that in addition to the above description and examples than as specifically described, the present invention can also be achieved in other ways. Other aspects within the scope of the invention and improvement of the present invention will be apparent to the ordinary skilled in the art. According to the teachings of the present invention, many modifications and variations are possible, and therefore it is within the scope of the present invention.

Unless otherwise indicated herein, the temperature unit "degrees" refers to Celsius, namely ° C.

What is claimed is:
1. A compound of formula

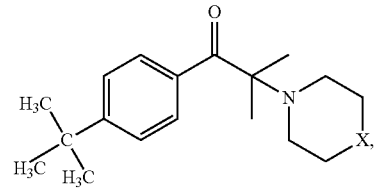

wherein X is C or O.

2. A photopolymerizable composition comprising:
  (a) a compound of claim 1 as a photoinitiator;
  (b) at least one ethylenically unsaturated photopolymerizable compound.
3. The photopolymerizable composition according to claim 2, wherein said ethylenically unsaturated photopolymerizable compound (b) is an ester of ethylenically unsaturated carboxylic acids and polyols or polyepoxides.
4. The photopolymerizable composition according to claim 2, which further comprises a reactive amine co-initiator (c) said amine co-initiator (c) is about 0.5-10% by weight based on the weight of the composition.
5. The photopolymerizable composition according to claim 2 comprising:
  epoxy acrylate about 35-55%
  amine co-initiator about 6-10%
  trimethylolpropane triacrylate about 29-56%
  photoinitiator about 3-6%.

6. The photopolymerizable composition according to claim 2, wherein the photoinitiator is about 0.5-10% by weight based on the weight of the composition.

7. The photopolymerizable composition according to claim 4, wherein said amine co-initiator (c) is about 6-10% by weight based on the weight of the composition.

\* \* \* \* \*